United States Patent
Sasso et al.

(10) Patent No.: US 7,354,442 B2
(45) Date of Patent: Apr. 8, 2008

(54) BONE ANCHOR AND METHODS OF USING THE SAME

(75) Inventors: Ricardo C. Sasso, Carmel, IN (US); Kevin T. Foley, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 420 days.

(21) Appl. No.: 10/429,430

(22) Filed: May 5, 2003

(65) Prior Publication Data

US 2004/0225292 A1   Nov. 11, 2004

(51) Int. Cl.
*A61B 17/58* (2006.01)

(52) U.S. Cl. ............... 606/73; 606/61; 606/92; 606/93

(58) Field of Classification Search ........... 606/72, 606/73, 99, 104, 86, 93, 92
See application file for complete search history.

(56) References Cited

U.S. PATENT DOCUMENTS

| | | | |
|---|---|---|---|
| 2,242,003 A | 5/1941 | Lorenzo | |
| 2,414,882 A | 1/1947 | Longfellow | |
| 4,383,527 A | 5/1983 | Asnis et al. | |
| 4,484,570 A * | 11/1984 | Sutter et al. | 606/72 |
| 4,537,185 A | 8/1985 | Stednitz | |
| 4,653,489 A | 3/1987 | Tronzo | |
| 4,913,134 A | 4/1990 | Luque | |
| 5,047,030 A | 9/1991 | Draenert | |
| 5,192,282 A | 3/1993 | Draenert | |
| 5,653,710 A | 8/1997 | Harle | |
| 5,743,912 A * | 4/1998 | Lahille et al. | 606/65 |
| 5,810,817 A | 9/1998 | Roussouly et al. | |
| 5,871,484 A | 2/1999 | Spievack et al. | |
| 6,048,343 A | 4/2000 | Mathis et al. | |
| 6,210,376 B1 | 4/2001 | Grayson | |
| 6,214,012 B1 | 4/2001 | Karpman et al. | |
| 6,235,028 B1 | 5/2001 | Brumfield et al. | |
| 6,287,313 B1 | 9/2001 | Sasso | |
| 6,517,542 B1 * | 2/2003 | Papay et al. | 606/73 |
| 6,554,830 B1 * | 4/2003 | Chappius | 606/61 |
| 6,562,041 B1 * | 5/2003 | Yonemura et al. | 606/61 |
| 2001/0021852 A1 | 9/2001 | Chappuis | |
| 2002/0082600 A1 | 6/2002 | Shaolian | |
| 2002/0123752 A1 * | 9/2002 | Schultheiss et al. | 606/73 |
| 2003/0065361 A1 | 4/2003 | Dreyfuss | |
| 2005/0055026 A1 * | 3/2005 | Biedermann et al. | 606/73 |

FOREIGN PATENT DOCUMENTS

| | | |
|---|---|---|
| DE | 1999 49 285 | 5/2001 |
| EP | 0 451 932 A | 10/1991 |
| EP | 0 504 915 A | 9/1992 |
| WO | WO 95/35180 A1 | 12/1995 |
| WO | WO 01/41681 A1 | 6/2001 |
| WO | WO 01/76494 A | 4/2003 |

* cited by examiner

*Primary Examiner*—Eduardo C. Robert
*Assistant Examiner*—Mary Hoffman
(74) *Attorney, Agent, or Firm*—Krieg DeVault LLP (57) ABSTRACT

A bone anchor including a bone engaging portion and an elongate guiding portion. In one embodiment, the bone engaging portion includes a cannula passage extending at least partially through the bone engaging portion, and at least one transverse opening in communication with the cannula passage. The elongate guiding portion extends from the bone engaging portion and is configured to guide a device into engagement with the bone engaging portion.

44 Claims, 7 Drawing Sheets

BONE ANCHOR AND METHODS OF USING THE SAME

FIELD OF THE INVENTION

The present invention generally relates to an improved bone anchor and methods of using the same.

SUMMARY OF THE INVENTION

In one form of the invention, a bone anchor is provided comprising a bone engaging portion and an elongate guiding portion. The bone engaging portion includes a cannula passage extending at least partially therethrough and at least one transverse opening in communication with the cannula passage. The elongate guiding portion extends from the bone engaging portion and is configured to guide a device into engagement with the bone engaging portion.

In another form of the invention, a bone anchor is provided comprising a bone engaging portion and means for guiding a device into engagement with the bone engaging portion. The bone engaging portion includes means for delivering material to a location laterally adjacent thereto.

In another form of the invention, a bone anchor is provided comprising a bone engaging portion and an elongate guiding portion adapted to engage the bone engaging portion so as to allow angular displacement relative thereto, with the elongate guiding portion being configured to guide a device into engagement with the bone engaging portion.

In another form of the invention, a surgical method is provided comprising providing a bone anchor having a bone engaging portion and an elongate guiding portion extending therefrom, anchoring- the bone engaging portion to bone, and guiding a device along the elongate guiding portion and into engagement with the bone engaging portion.

In another form of the invention, a surgical method is provided comprising providing a bone anchor having a bone engaging portion including a cannula passage extending at least partially therethrough and at least one transverse opening in communication with the cannula passage, anchoring the bone engaging portion to a vertebral body with the at least one transverse opening positioned adjacent a facet capsule of the vertebral body, delivering a material through the cannula passage, and dispensing the material out the at least one transverse opening and into the facet capsule.

It is one object of the present invention to provide an improved bone anchor and methods of using the same.

Further objects, features, advantages, benefits, and further aspects of the present invention will become apparent from the drawings and description contained herein.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Figure 1:
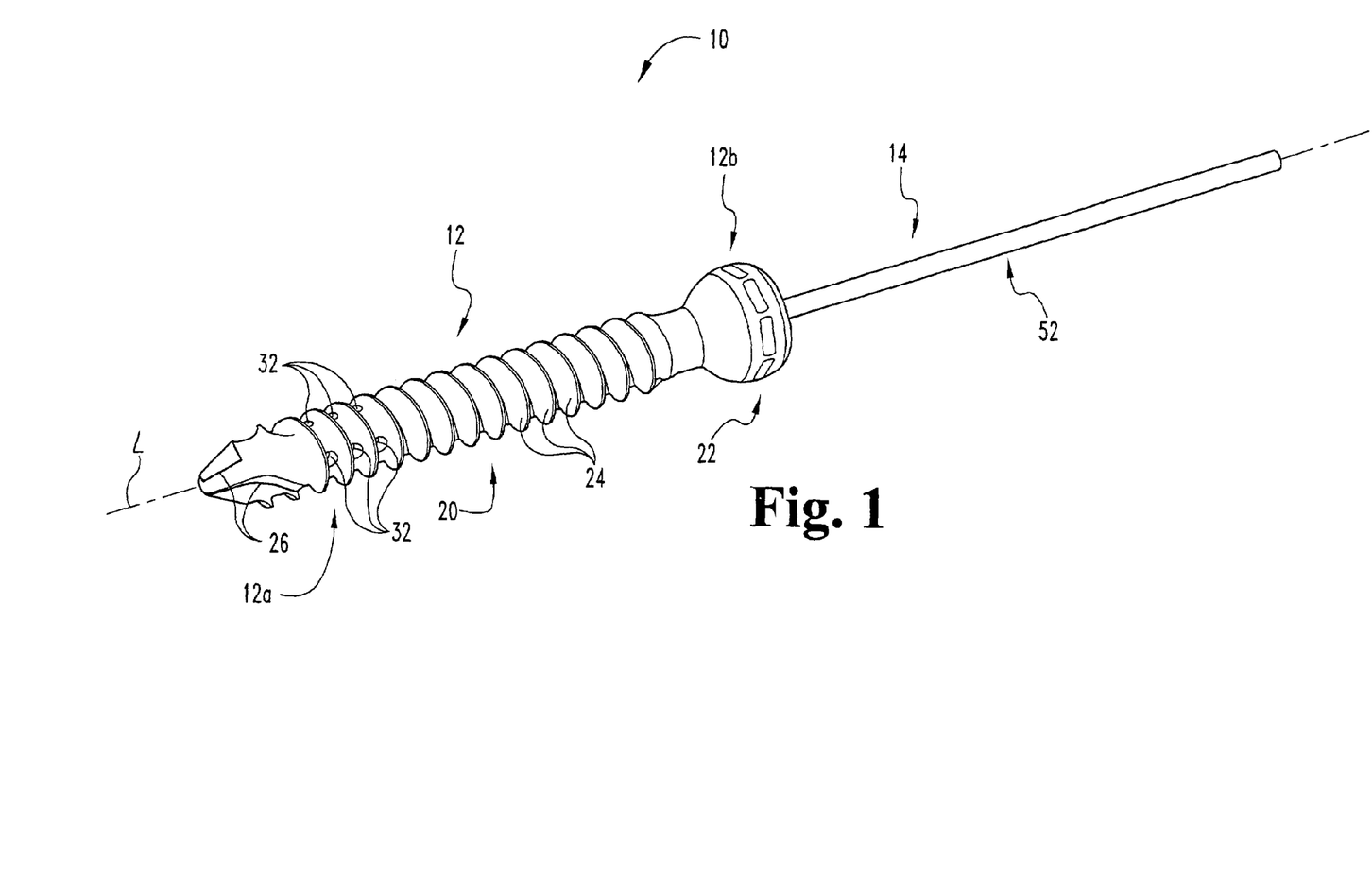
FIG. 1 is a perspective view of a bone anchor according to one form of the present invention.

Referring to FIG. 1, shown therein is a bone anchor 10 according to one form of the present invention. The bone anchor 10 is generally comprised of a bone engaging portion 12 and an elongate guiding portion 14. As will be discussed in further detail below, the bone engaging portion 12 is adapted for anchoring to bone. In one embodiment, the bone engaging portion 12 is adapted for anchoring to vertebral bone. However, it should be understood that the bone anchor 10 may be used in association with other skeletal members and in anatomical areas outside of the spinal column. The elongate guiding portion 14 extends from the bone engaging portion 12 and is adapted to guide or deliver various devices, materials, instruments, implants and/or other elements to the bone engaging portion 12. In one embodiment of the invention, the elongate guiding portion 14 is configured to releasably engage the bone engaging portion 12 so as to allow selective removal therefrom, the details of which will be discussed below.

In one embodiment of the invention, the bone engaging portion 12 comprises a bone screw extending generally along a longitudinal axis L between a distal end portion 12a and a proximal end portion 12b. The bone screw 12 generally includes a threaded shank portion 20 and a proximal head portion 22. However, it should be understood that the bone engaging portion 12 may take on other configurations, including non-threaded configurations, such as, for example, a hook configuration or any other configuration suitable for anchoring to bone as would occur to one of skill in the art. The threaded shank portion 20 defines external threads 24 configured to engage internal threads formed along a passage in the bone. In one embodiment, the threads 24 are cancellous threads configured to engage vertebral bone. However, it should be understood that other types and configurations of threads are also contemplated as falling within the scope of the present invention. The distal end of the threaded shank 20 may define one or more cutting flutes 26 extending across at least one of the threads 24 to provide the bone anchor 10 with self-tapping and/or self-cutting capabilities. The proximal head 22 preferably has a generally smooth outer surface that is devoid of sharp corners or edges to avoid trauma or irritation of adjacent tissue. In one embodiment, the proximal head 22 has a spherical-shaped configuration. However, other configurations are also contemplated, such as, for example, a conical or cylindrical configuration. The outer surface of the proximal head 22 may include a number of flattened areas (FIG. 1) for engagement with a driving tool.

Figure 2:
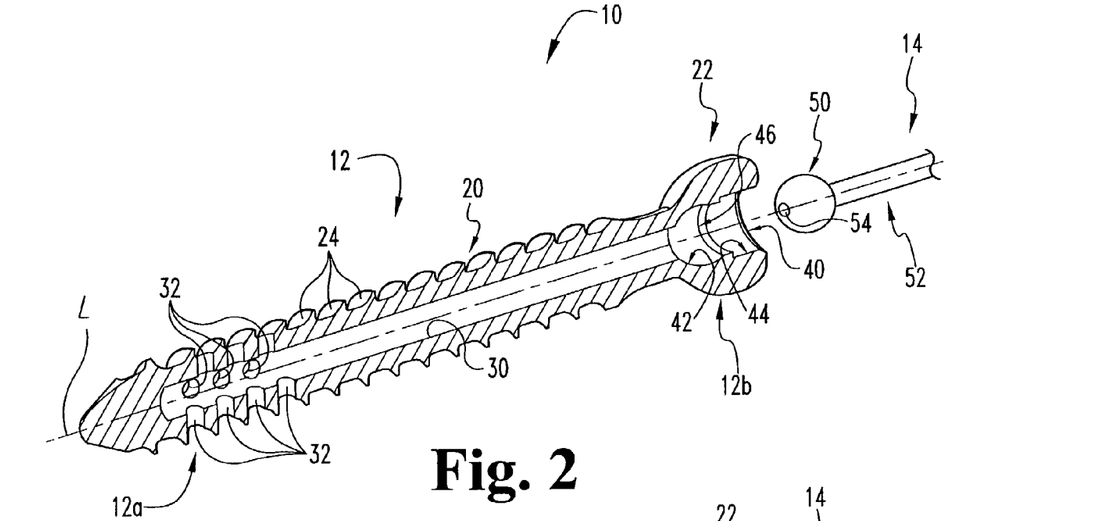
FIG. 2 is a partial cross-sectional exploded perspective view of the bone anchor illustrated in FIG. 1.
Figure 3:
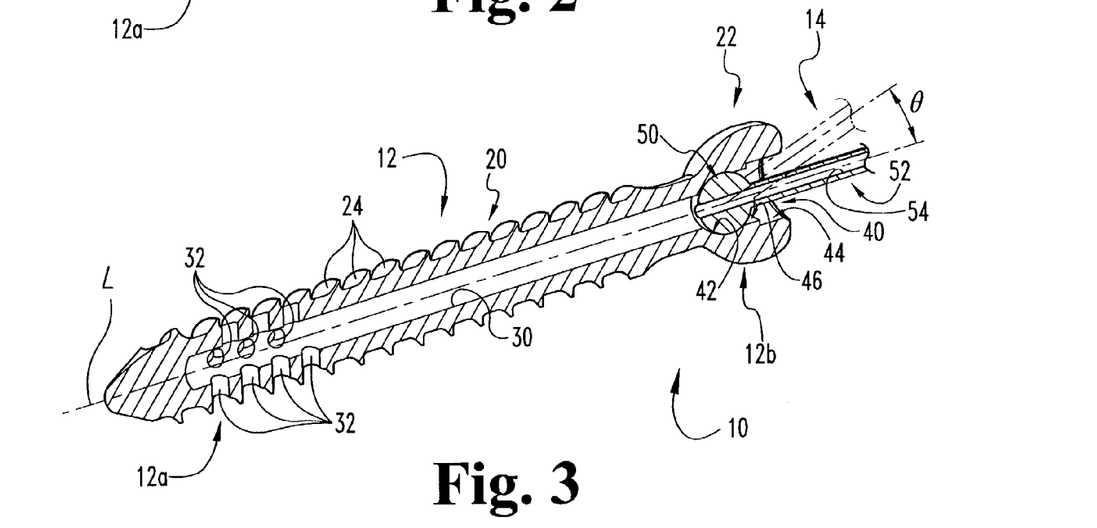
FIG. 3 is a cross-sectional perspective view of the bone anchor illustrated in FIG. 1.

Referring to FIGS. 2 and 3, in one embodiment of the invention, the bone engaging portion 12 of the bone anchor 10 defines a cannula passage 30 extending generally along the longitudinal axis L. Although the cannula passage 30 is illustrated as extending partially through the bone engaging portion 12 so as to define a partially-cannulated bone screw, it should be understood that in other embodiments of the invention, the cannula passage 30 may extend entirely through the bone engaging portion 12 so as to define a fully-cannulated bone screw.

In a further embodiment of the invention, the bone engaging portion 12 of the bone anchor 10 defines a number of fenestration openings 32 extending through the side wall of the bone engaging portion in a transverse direction and in communication with the axial cannula passage 30. In one embodiment of the invention, the transverse fenestration openings 32 are confined to the distal end portion 12a of the bone engaging portion 12, and in a more specific embodiment are disposed along the distal-most one-third of the bone engaging portion 12. However, it should be understood that in other embodiments of the invention, the fenestration openings 32 may be disposed along other portions of the bone engaging portion 12, including along the proximal portion 12b or along the entire length of the bone engaging portion 12.

As will be discussed in further detail below, the cannula passage 30 and the transverse fenestration openings 32 cooperate to deliver a material to select regions of the bone in which the bone engaging portion 12 is engaged. Such materials may include, for example, bone cement, a bone growth promoting material such as a bone morphogenic protein (BMP), or other bio-compatible materials. In embodiments of the invention utilizing a partially-cannulated bone screw, the entire amount of the material is delivered into the cannula passage 30 and out the transverse fenestration openings 32 in a lateral direction, with no material being discharged from the distal end of the bone engaging portion 12 in an axial direction. As a result, delivery of the material to select portions of the bone can be accomplished in a controlled and efficient manner, the details of which will be discussed below.

The proximal head 22 of the bone engaging portion 12 includes a shaped passage or recess 40 communicating with the cannula passage 30. The shaped recess 40 is configured to receive a shaped end portion of the elongate guiding portion 14 therein to couple the elongate guiding portion 14 with the bone engaging portion 12, the details of which will be discussed below. However, it should be understood that in an alternative embodiment of the invention, the proximal head 22 may comprise a shaped end portion that is receivable within a shaped passage or recess defined in the elongate guiding portion 14 to couple the elongate guiding portion 14 with the bone engaging portion 12.

In one embodiment of the invention, the shaped recess 40 defined in the proximal head 22 includes a connecting portion 42, a receiving portion 44, and a retaining portion 46 disposed between the connecting portion 42 and the receiving portion 44. In a specific embodiment, the connecting portion 42 comprises a spherical-shaped socket sized to engagingly receive a correspondingly shaped end portion of the guiding portion 14 therein to connect the guiding portion 14 to the bone engaging portion 12. In another specific embodiment, the receiving portion 44 comprises an axially-extending receptacle or opening sized to engagingly receive a corresponding end portion of an instrument, implant, mechanism, and/or other types of elements therein. The receiving portion 44 may take on a number of different shapes and configurations, including a hexagonal shape, a circular or elliptical shape, a square or rectangular shape, a Torx™-type configuration, or any other shape or configuration that would occur to one of skill in the art. In a further specific embodiment, the retention portion 46 comprises an annular shoulder extending between the socket 42 and the receptacle 44. The retention portion 46 defines an inner diameter sized somewhat smaller than the spherical-shaped socket 42 to retain a corresponding end portion of the guiding portion 14 therein. It should be understood, however, that other shapes, sizes and/or configurations of the connecting portion 42, receiving portion 44, and retaining portion 46 are also contemplated as falling within the scope of the present invention.

In one embodiment of the invention, the elongate guiding portion 14 comprises a shaped end portion 50 and an elongate shaft portion 52 extending therefrom. In a specific embodiment, the shaped end portion 50 has a ball or spherical-shaped configuration corresponding to the size and shape of the spherical-shaped socket 42 defined by the shaped recess 40 in the proximal head 22 of the bone engaging portion 12. In a specific embodiment, the spherical shaped ball 50 has an outer diameter sized in close tolerance with the inner diameter of the spherical-shaped socket 42 so as to provide a relatively close fit therebetween while still allowing the ball 50 to freely rotate within the socket 42. Although the shaped recess 42 and the shaped end portion 50 are illustrated and described as having spherical configurations, it should be understood that other shapes and configurations are also contemplated as falling within the scope of the present invention, examples of which will be illustrated and described below.

In a further embodiment of the invention, the shaped end portion 50 is engagingly received within the shaped recess 42 in a manner allowing selective removal of the elongate guiding portion 14 from the bone engaging portion 12. In one embodiment, the annular shoulder 46 positioned adjacent the spherical-shaped socket 42 has an inner diameter sized somewhat smaller than the outer diameter of the spherical-shaped ball portion 50. As a result, the annular shoulder 46 serves to selectively retain the ball portion 50 within the socket 42, which in turn selectively engages the elongate guiding portion 14 with the bone engaging portion 12. Since the annular shoulder 46 is sized somewhat smaller than the ball portion 50, in one embodiment of the invention, the ball portion 50 is press fit into the socket 42. As a result, the annular shoulder 46 and/or the ball portion 50 are slightly deformed during insertion and removal of the ball portion 50 into/from the socket 42.

Referring specifically to FIG. 3, in the illustrated embodiment of the invention, the ball portion 50 is engaged within the socket 42 so as to allow angular displacement of the elongate guiding portion 14 relative to the bone engaging portion 12 up to a displacement angle θ (as measured relative to the longitudinal axis L). In one embodiment, the ball portion 50 and the socket 42 cooperate to provide the bone anchor 10 with multi-axial capabilities, allowing angular displacement of the elongate guiding portion 14 in multiple directions relative to the bone engaging portion 12 up to the displacement angle θ. In a specific embodiment of the invention, the displacement angle θ falls within a range of about 5 degrees to about 30 degrees. However, it should be understood that other displacement angles θ are also contemplated as falling within the scope of the present invention. It should also be understood that the ball portion 50 and the socket 42 may cooperate to limit or prohibit angular displacement of the elongate guiding portion 14 relative to the bone engaging portion 12 in one or more directions.

The elongate shaft portion 52 extends from the ball portion 50 and is adapted to guide or direct various devices, instruments, implants and/or other elements toward the proximal head 22 of the bone engaging portion 12, the details of which will be discussed below. In one embodiment of the invention, the elongate shaft portion 52 is flexible so as to allow the elongate shaft portion 52 to be reshaped or bent either before or during displacement of the devices, instruments, implants and/or other elements toward the proximal head 22 of the bone engaging portion 12. However, it should be understood that the elongate shaft portion 52 may alternatively have a substantially rigid configuration so as to prevent or resist deflection of the elongate shaft portion 52 during displacement of the devices, instruments, implants and/or other elements toward the proximal head 22 of the bone engaging portion 12.

In one embodiment of the invention, the elongate shaft portion 52 is at least partially formed of a flexible, malleable or pliable material to allow for reshaping or bending. Such material may include, for example, an aluminum material, a shape-memory material, a plastic material, or certain types of stainless steel or titanium. If a relatively soft material is used, such as an aluminum material, the elongate shaft portion 52 may be covered with a protective coating such as an anodized oxide film or one or more layers of an elastomeric polymer such as Teflon. In another embodiment of the invention, the elongate shaft portion 52 is formed of a substantially rigid or non-malleable material, such as, for example, stainless steel or titanium. The use of a rigid material allows the elongate shaft portion 52 to maintain a predetermined shape or configuration.

If the elongate shaft portion 52 is at least partially formed of a shape-memory alloy (SMA), the elongate shaft portion 52 may be bent or reshaped from an initial configuration to a different configuration and automatically reformed back toward the initial configuration without having to manually bend the elongate shaft portion 52 back toward its initial configuration. This shape-memory characteristic occurs when the SMA is transformed from a martensitic crystal phase to an austenitic crystal phase. This phase transformation can occur with or without a corresponding change in temperature. Further details regarding the features and characteristics of SMA materials are more fully described in U.S. Pat. No. 5,551,871 to Besselink and in U.S. Pat. No. 5,597,378 to Jervis, the contents of which are hereby incorporated by reference.

As illustrated in FIG. 3, in a further embodiment of the invention, an axial passageway 54 extends along the elongate shaft portion 52 and through the shaped end portion 50, thereby defining a fully-cannulated elongate guiding portion 14. However, it should be understood that the shaped end portion 50 and the elongate shaft portion 52 need not necessarily define an axial passageway 54, but may instead define a solid, non-cannulated elongate guiding portion 14. When the ball portion 50 of the elongate guiding portion 14 is disposed within the shaped recess 40 of the bone engaging portion 12, the axial passageway 54 is disposed in fluid communication with the cannula passage 30. In this manner, various materials may be delivered through the axial passageway 54 from a location remote from the bone engaging portion 12 and into the cannula passage 30 for distribution to the transverse fenestration openings 32. As discussed above, such materials may include bone cement or a bone growth promoting material such as BMP.

Figure 4:
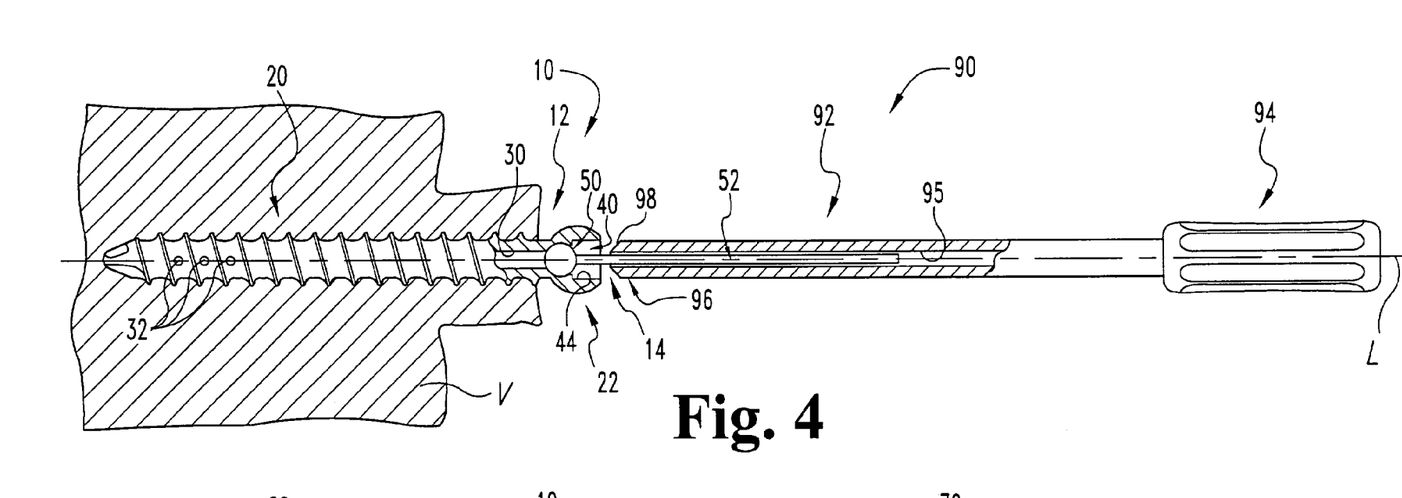
FIG. 4 is a partial cross-sectional side view of the bone anchor illustrated in FIG. 1, as engaged within a skeletal member and with a surgical instrument being guided toward the bone engaging portion of the bone anchor along an elongate guiding portion of the bone anchor.
Figure 5:
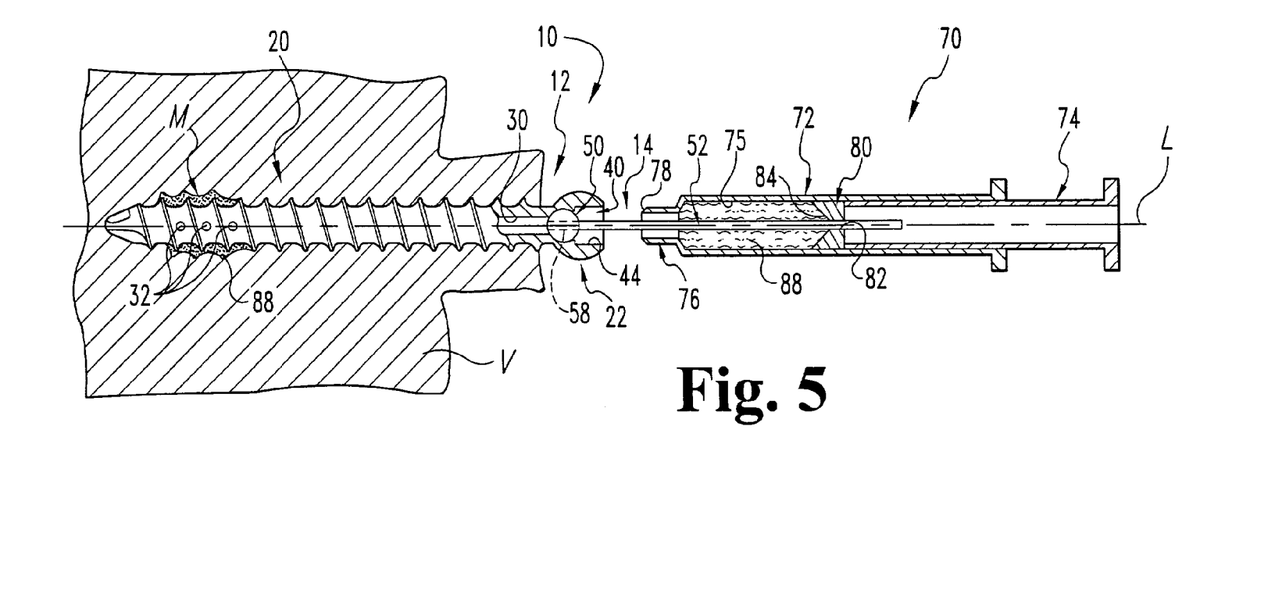
FIG. 5 is a partial cross-sectional side view of the bone anchor illustrated in FIG. 1, as engaged within a skeletal member and with an injector mechanism being guided toward the bone engaging portion of the bone anchor along an elongate guiding portion of the bone anchor.

Referring to FIGS. 4 and 5, shown therein are two specific applications of the bone anchor 10. However, it should be understood that the applications illustrated in FIGS. 4 and 5 are exemplary and that other applications and uses of the bone anchor 10 are also contemplated as falling within the scope of the present invention. In the illustrated embodiments of the invention, the bone engaging portion 12 of the bone anchor 10 is anchored to the vertebra V with the elongate guiding portion 14 extending from the proximal head 22. As mentioned above, the distal end portion of the threaded shank 20 may define one or more cutting flutes 26 to provide the bone engaging portion 12 with self-tapping and/or self-cutting capabilities to facilitate insertion of the bone engaging portion 12 into the vertebra V.

In one embodiment of the invention, the elongate shaft 52 has a length such that at least the proximal end portion of the elongate shaft 52 extends outside of the patient's body when the bone engaging portion 12 is anchored to bone, such as, for example, to the vertebra V. As a result, various types of devices, instruments, implants and/or other elements may be advanced along the elongate shaft 52 from a location outside of the patient's body to a location adjacent the proximal head 22 of the bone engaging portion 12. In some embodiments of the invention, such devices, instruments, implants and/or other elements are slidingly advanced along the length of the elongate shaft 52 toward the bone engaging portion 12. However, other methods of advancement along the length of the elongate shaft 52 are also contemplated as falling within the scope of the present invention. Following the positioning, delivery and/or use of the device, instrument, implant and/or other elements adjacent the proximal head 22 of the bone anchor 10, the elongate guiding portion 14 may be selectively removed from the bone engaging portion 12 to provide a low profile anchoring structure.

Referring specifically to FIG. 4, in one embodiment of the invention, the elongate shaft 52 of the guiding portion 14 is sized and configured to slidably engage a surgical instrument 90 to guide the distal end portion of the instrument 90 into engagement with the proximal head 22 of the bone engaging portion 12. In the illustrated embodiment, the surgical instrument 90 is configured as a driver instrument generally comprised of a shaft 92 and a handle 94. However, it should be understood that other types and configurations of instruments may be used in association with the present invention. The shaft 92 defines an axial passage 95 extending at least partially therethrough and sized to receive the elongate shaft 52 of the guiding portion 14 therein.

The distal end portion 96 of the shaft 92 is preferably sized and configured for engagement within the receiving portion 44 defined by the proximal head 22 of the bone anchor 10 to facilitate driving of the bone engaging portion 12 into and/or out of bone. As mentioned above, the receiving portion 44, and likewise the distal end portion 96 of the instrument shaft 92, may take on a number of different shapes and configurations, including a hexagonal shape, a circular or elliptical shape, a square or rectangular shape, a Torx™-type configuration, or any other shape or configuration that would occur to one of skill in the art. The distal-most end of the shaft 92 may define a tapered surface 98 to aid in insertion of the distal end portion 96 into the receiving portion 44 of the proximal head 22. In other embodiments of the invention, the distal end portion of the instrument 90 may be configured with a receptacle or socket-type fitting for engagement over the proximal head 22 of the bone engaging portion 12 to facilitate driving of the bone engaging portion 12 into and/or out of bone.

As should be appreciated, the driver instrument 90 may be engaged with the proximal end portion of the elongate shaft 52 at a location outside of the patient's body via insertion of the proximal end portion of the shaft 52 into the axial passage 95 defined within the driver shaft 92. The elongate shaft 52 may then be used to guide the driver instrument 90 through a visually-obstructed opening, such as, for example a relatively small access portal (not shown) in the patient's skin or other bodily tissue and/or through a relatively narrow tissue protection device, such as, for example, a cannula tube, to facilitate engagement of the distal end portion 96 of the instrument 90 with the proximal head 22 of the bone anchor 10. As discussed above, the elongate guiding portion 14 is engaged with the bone engaging portion 12 in such a manner as to allow angular displacement of the elongate guiding portion 14 relative to the bone engaging portion 12 (FIG. 3). As a result, guidance of the driver instrument 90 toward the proximal head 22 of the bone anchor 10 in directions transverse to the longitudinal axis L is possible. In other words, displacement of the driver instrument 90 does not necessarily have to occur along the longitudinal axis L. Instead, the instrument 90 may be guided toward the proximal head 22 of the bone engaging portion 12 in angular directions relative to the longitudinal axis L, up to and including the displacement angle θ illustrated in FIG. 3.

Referring to FIG. 5, in a further embodiment of the invention, the guiding portion 14 of the bone anchor 10 is used to guide an injector or delivery mechanism 70 into engagement with the proximal head 22 of the bone engaging portion 12. The injector mechanism 70 is in turn configured to deliver a material into the cannula passage 30 of the bone engaging portion 12, out the transverse fenestration openings 32, and into the surrounding bone tissue, the details of which will be discussed below. In the illustrated embodiment, the injector mechanism 70 is configured as a syringe. However, other types and configurations of mechanisms, devices and systems for injecting or delivering a material into the cannula passage 30 and out the transverse openings 32 are also contemplated as would occur to one of skill in the art.

The injector mechanism 70 generally includes a receptacle portion 72 and a plunger portion 74. The receptacle portion 72 defines a hollow interior 75 for receiving an amount of material 88 therein. The receptacle portion 74 also includes a distal tip portion 76 that is sized and configured for engagement within the receiving portion 44 defined within the proximal head 22 of the bone anchor 10 to facilitate delivery of the material 88 into the cannula passage 30. As mentioned above, the receiving portion 44, and likewise the distal tip portion 76 of the injector mechanism 70, may take on a number of different shapes and configurations, including a hexagonal shape, a circular or elliptical shape, a square or rectangular shape, or any other shape or configuration that would occur to one of skill in the art. The distal-most end of the tip portion 76 may define a tapered surface 78 to aid in the insertion of the tip portion 76 into the receiving portion 44 of the proximal head 22. In other embodiments of the invention, the distal end portion of the injector mechanism 70 may be configured with a receptacle or socket-type fitting for engagement over the proximal head 22 of the bone engaging portion 12 to facilitate delivery of the material 88 into the cannula passage 30.

The plunger portion 74 of the injector mechanism 70 includes a main body portion that is sized and shaped for displacement along the hollow interior 75 of the receptacle portion 72 to inject the material 88 into the cannula passage 30 of the bone anchor 10. The plunger portion 74 includes an end portion 80 that functions in a piston-like manner to force the material 88 through the hollow interior 75 of the receptacle 72, out the tip portion 76, and into the cannula passage 30. The end portion 80 of the plunger 74 defines an axial passage 82 extending therethrough that is sized and shaped to receive the elongate shaft 52 of the guiding portion 14 therein. The distally-facing surface 84 of the end portion 80 may be inwardly tapered toward the axial passage 82 to aid in the insertion of the elongate shaft 52 into the axial passage 82.

As should be appreciated, the injector mechanism 70 may be engaged with the proximal end portion of the elongate shaft 52 at a location outside of the patient's body via insertion of the proximal end portion of the shaft 52 through the tip portion 76 and into the hollow interior 75 of the receptacle 72. If required, the proximal end portion of the shaft 52 may also be inserted into the axial passage 82 defined by the end portion 80 of the plunger 74. The elongate shaft 52 may then be used to guide the injector mechanism 70 through a visually-obstructed opening and/or through a relatively narrow tissue protection device to facilitate engagement of the distal end portion 76 of the injector mechanism 70 with the proximal head 22 of the bone anchor 10. As discussed above, the elongate guiding portion 14 is engaged with the bone engaging portion 12 in such a manner as to allow angular displacement of the elongate guiding portion 14 relative to the bone engaging portion 12. As a result, guidance of the injector mechanism 70 toward the proximal head 22 of the bone anchor 10 in directions transverse to the longitudinal axis L is possible.

Following insertion of the tip portion 76 into the receiving portion 44 of the proximal head 22, the plunger 74 is displaced along the hollow interior 75 of the receptacle 72 to force the material 88 out of the tip portion 76. The spherical-shaped end portion 50 of the elongate guiding portion 14 may include one or more passages 58 extending therethrough to provide communication between the receiving portion 44 of the passage 40 and the cannula passage 30 to facilitate delivery of the material 88 into the cannula passage 30. The material 88 is in turn conveyed through the cannula passage 30 and is dispensed out of the transverse fenestration openings 32 to a location laterally adjacent the bone engaging portion 12 of the bone anchor 10. In an alternative embodiment of the invention, the material 88 may be delivered to the cannula passage 30 via an axial passageway 54 extending through the elongate guiding portion 14 (FIGS. 2 and 3) of the bone anchor 10. In this manner, the material 88 may be conveyed through the axial passageway 54 and delivered to the cannula passage 30 via a delivery system or injector mechanism located remote from the proximal head 22 of the bone engaging portion 12, and possibly from a location entirely outside of the patient's body.

As discussed above, various materials may delivered via the bone engaging portion 12 of the bone anchor 10, such as, for example, bone cement, a bone growth promoting material, or other bio-compatible materials. In the embodiment of the invention illustrated in FIG. 5, the material 88 delivered into the bone engaging portion 12 via the injector mechanism 70 is bone cement. Following dispersion of the material 88 out the transverse fenestration openings 32, the cement material 88 cures or hardens, thereby forming a mantle M of material about the threaded shank 20. The mantle M of material serves to enhance engagement of the bone engaging portion 12 to the vertebra V, thereby preventing or at least substantially resisting bone anchor pull-out. In embodiments of the invention where the material 88 comprises a bone growth promoting material such as BMP, the bone growth promoting material may similarly be delivered into the cannula passage 30 and out the fenestration openings 32 to promote bone growth in areas laterally adjacent the threaded shank 20 of the bone anchor 10.

As indicated above, in the illustrated embodiment of the bone anchor 10, each of the fenestration openings 32 are disposed along the distal end portion of the threaded shank 20, and more particularly along the distal-most one-third of the threaded shank 20, thereby limiting formation of the mantle M of material about the distal end portion of the threaded shank 20. Additionally, since the cannula passage 30 does not extend entirely through the bone engaging portion 12, the entire amount of the material 88 is dispersed out the transverse fenestration openings 32 in a lateral direction, with no material 88 being discharged from the distal end of the bone engaging portion 12 in an axial direction.

Figure 6:
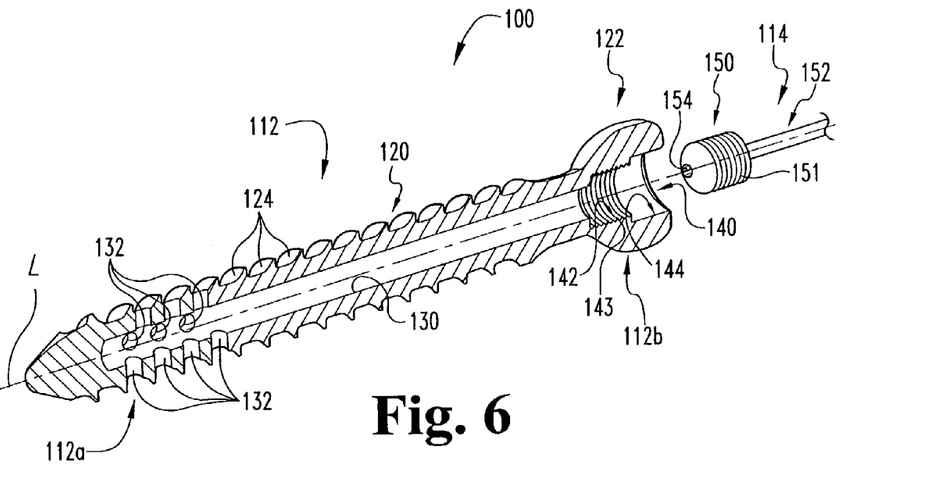
FIG. 6 is a partial cross-sectional exploded perspective view of a bone anchor according to another form of the present invention.

Referring to FIG. 6, shown therein is a bone anchor 100 according to another form of the present invention. In many ways, the bone anchor 100 is configured similar to the bone anchor 10 illustrated and described above, generally comprising a bone engaging portion 112 and an elongate guiding portion 114 adapted to guide or deliver various devices, materials, instruments, implants and/or other elements to the bone engaging portion 112. Similar to the bone engaging portion 12, the bone engaging portion 112 comprises a bone screw having a distal end portion 112a and a proximal end portion 112b, and includes a threaded shank portion 120 and a proximal head portion 122. The threaded shank portion 120 defines external threads 124 configured to engage internal threads formed along a passage in bone. Additionally, the bone engaging portion 112 defines a cannula passage 130 extending axially from the proximal end portion 112b toward the distal end portion 112a, and a number of transverse fenestration openings 132 in communication with the cannula passage 130 and positioned along the distal end portion 112a.

The proximal head 122 of the bone engaging portion 112 includes a shaped passage or recess 140 communicating with the cannula passage 130. The shaped recess 140 is configured to receive a correspondingly shaped end portion of the elongate guiding portion 114 therein to selectively couple the elongate guiding portion 114 with the bone engaging portion 112, the details of which will be discussed below. In one embodiment of the invention, the shaped recess 140 defined in the proximal head 122 includes a connecting portion 142 and a receiving portion 144. In a specific embodiment, the connecting portion 142 comprises a cylindrical-shaped passage sized to engagingly receive an end portion of the guiding portion 114 therein. In a further embodiment, the cylindrical-shaped passage 142 defines internal threads 143 adapted to threadingly engage an end portion of the guiding portion 114. In another specific embodiment, the receiving portion 144 comprises an axially-extending receptacle or opening sized to engagingly receive a corresponding end portion of an instrument, implant, mechanism, and/or other types of elements therein, examples of which have been illustrated and described above with regard to the bone anchor 10.

In one embodiment of the invention, the elongate guiding portion 114 comprises a shaped end portion 150 and an elongate shaft portion 152 extending therefrom. In the illustrated embodiment, the shaped end portion 150 has a cylindrical-shaped configuration defining external threads 151 adapted for engagement within the internally threaded passage 142 defined in the proximal head 122 of the bone engaging portion 112. As should be appreciated, the threading engagement between the externally threaded end portion 150 and the internally threaded passage 142 releasably engages the elongate guiding portion 114 to the bone engaging portion 112 and also allows for selective removal of the elongate guiding portion 114 therefrom. The distally-facing surface of the threaded end portion 150 may be tapered to facilitate insertion into and threading engagement with the internally threaded passage 142.

Similar to the elongate shaft portion 52 illustrated and described above with regard to the bone anchor 10, the elongate shaft portion 152 extends from the threaded end portion 150 and is adapted to guide or direct various devices, instruments, implants and/or other elements toward the proximal head 122 of the bone engaging portion 112. In the illustrated embodiment of the bone anchor 100, an axial passageway 154 extends along the elongate shaft portion 152 and through the threaded end portion 150 to allow delivery of a material to the cannula passage 130 from a location remote from the bone engaging portion 112 for distribution out of the transverse fenestration openings 132.

Figure 7:
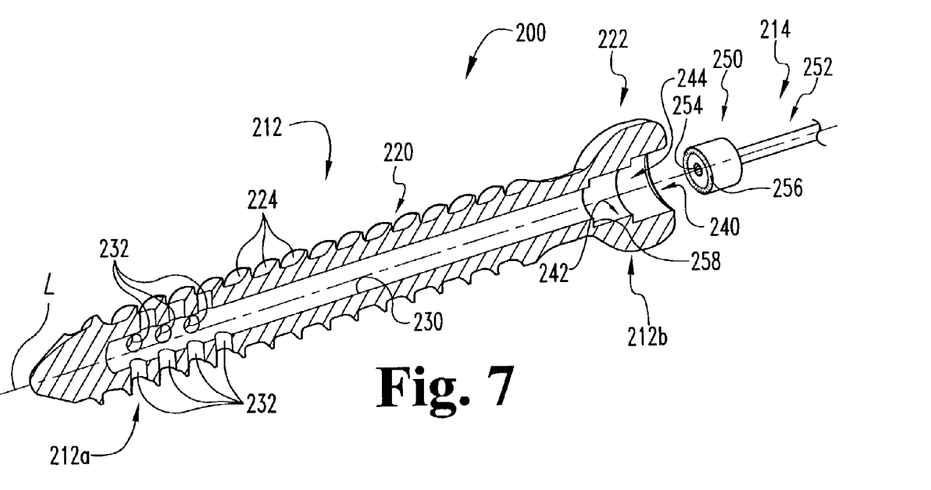
FIG. 7 is a partial cross-sectional exploded perspective view of a bone anchor according to still another form of the present invention.

Referring to FIG. 7, shown therein is a bone anchor 200 according to another form of the present invention. In many ways, the bone anchor 200 is configured similar to the bone anchor 100 illustrated and described above, generally comprising a bone engaging portion 212 and an elongate guiding portion 214 adapted to guide or deliver various devices, materials, instruments, implants and/or other elements to the bone engaging portion 212. The bone engaging portion 212 comprises a bone screw having a distal end portion 212a and a proximal end portion 212b, and includes a threaded shank portion 220 and a proximal head portion 222. The threaded shank portion 220 defines external threads 224 configured to engage internal threads formed along a passage in bone. Additionally, the bone engaging portion 212 defines a cannula passage 230 extending axially from the proximal end portion 212b toward the distal end portion 212a, and a number of transverse fenestration openings 232 in communication with the cannula passage 230 and positioned along the distal end portion 212a.

The proximal head 222 of the bone engaging portion 212 includes a shaped passage or recess 240 communicating with the cannula passage 230. The shaped recess 240 is configured to receive a correspondingly shaped end portion of the elongate guiding portion 214 therein to selectively couple the elongate guiding portion 214 with the bone engaging portion 212. In one embodiment of the invention, the shaped recess 240 defined in the proximal head 222 includes a connecting portion 242 and a receiving portion 244. In a specific embodiment, the connecting portion 242 comprises a cylindrical-shaped passage sized to engagingly receive a correspondingly shaped end portion of the guiding portion 214 therein. In another specific embodiment, the receiving portion 244 comprises an axially-extending receptacle or opening sized to engagingly receive a corresponding end portion of an instrument, implant, mechanism, and/or other types of elements therein, examples of which have been illustrated and described above with regard to the bone anchor 10.

In one embodiment of the invention, the elongate guiding portion 214 comprises a shaped end portion 250 and an elongate shaft portion 252 extending therefrom. In the illustrated embodiment, the shaped end portion 250 has a cylindrical-shaped configuration sized and shaped for releasable engagement within the cylindrical-shaped passage 242 defined in the proximal head 222 of the bone engaging portion 212 and allowing for selective removal of the elongate guiding portion 214 therefrom.

Similar to the elongate shaft portion 52 illustrated and described above with regard to the bone anchor 10, the elongate shaft portion 252 extends from the shaped end portion 250 and is adapted to guide or direct various devices, instruments, implants and/or other elements toward the proximal head 222 of the bone engaging portion 212. In the illustrated embodiment of the bone anchor 200, an axial passageway 254 extends along the elongate shaft portion 252 and through the shaped end portion 250 to allow delivery of a material to the cannula passage 230 from a location remote from the bone engaging portion 212 for distribution out of the transverse fenestration openings 232. A seal 256 may be engaged between the shaped end portion 250 of the elongate guiding portion 214 and the proximal head 222 of the bone engaging portion 212 to provide a fluid-tight seal therebetween. In a specific embodiment, the seal 256 comprises an O-ring disposed between a distally-facing surface of the shaped end portion 250 and an annular shoulder 258 located at the bottom of the cylindrical-shaped passage 242 of the recess 240. In a further embodiment, the distally-facing surface of the shaped end portion 250 and/or the annular shoulder 258 may define an annular retention groove (not shown) sized and shaped to receive the O-ring 256 therein to maintain the O-ring 256 in the proper position. In other embodiments of the invention, a seal may be positioned about the periphery of the shaped end portion 250 to provide a fluid-tight seal between the guiding portion 214 and the bone engaging portion 212.

Referring to FIGS. 8-11, shown therein is a bone anchor 300 according to another form of the present invention. In many ways, the bone anchor 300 is configured similar to the bone anchor 100 illustrated and described above, generally comprising a bone engaging portion 312 and an elongate guiding portion 314 adapted to guide or deliver various devices, materials, instruments, implants and/or other elements to the bone engaging portion 312. Similar to the bone engaging portion 112, the bone engaging portion 312 comprises a bone screw having a distal end portion 312a and a proximal end portion 312b, and includes a threaded shank portion 320 and a proximal head portion 322. The threaded shank portion 320 defines external threads 324 configured to engage internal threads formed along a passage in bone. Additionally, the bone engaging portion 312 defines a cannula passage 330 extending axially from the proximal end portion 312b toward the distal end portion 312a, and a number of transverse fenestration openings 332 in communication with the cannula passage 330 and positioned along the distal end portion 312a.

Figures 8, 9:
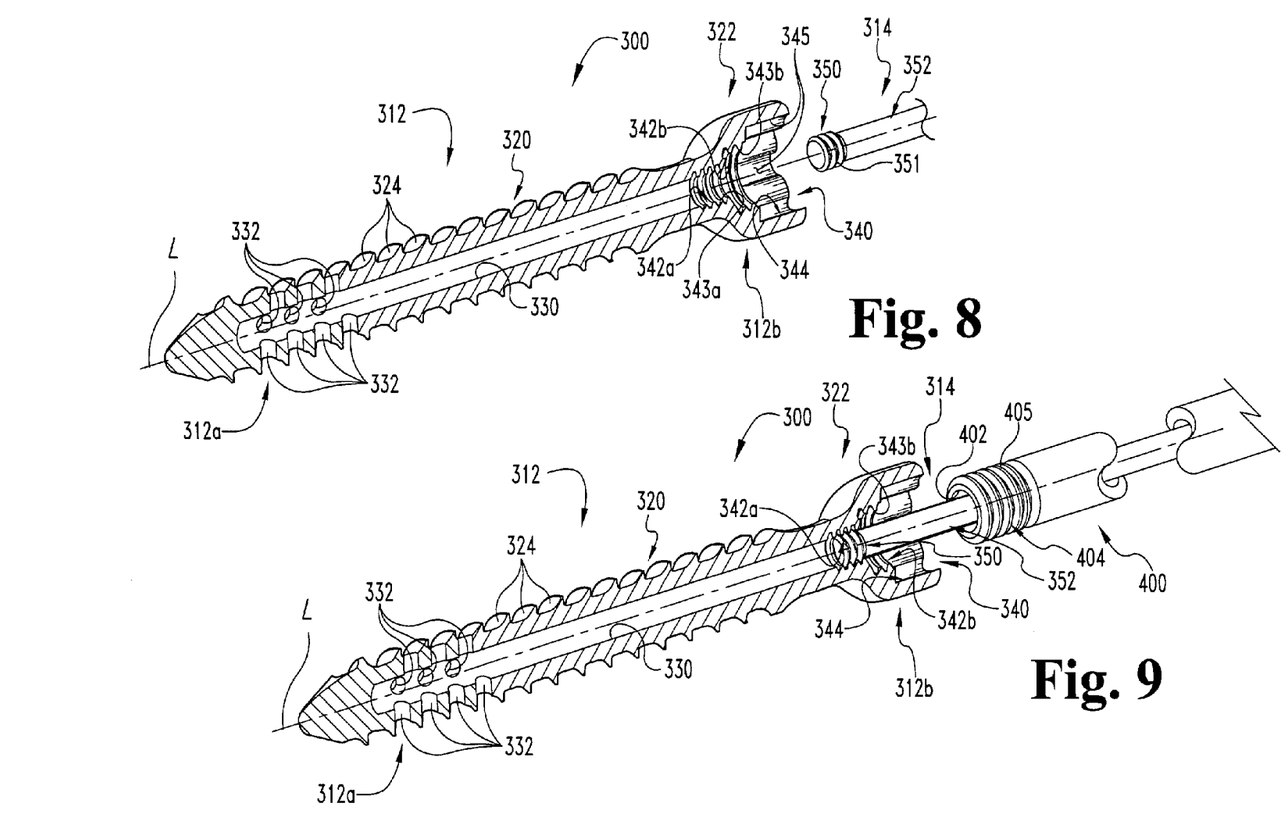
FIG. 8 is a partial cross-sectional exploded perspective view of a bone anchor according to yet another form of the present invention.
FIG. 9 is a partial cross-sectional perspective view of the bone anchor illustrated in FIG. 8, with an injector tube being guided toward the bone engaging portion of the bone anchor along an elongate guiding portion of the bone anchor.

The proximal head 322 of the bone engaging portion 312 includes a shaped passage or recess 340 communicating with the cannula passage 330. The shaped recess 340 is configured to receive a correspondingly shaped end portion of the elongate guiding portion 314 therein to selectively couple the elongate guiding portion 314 with the bone engaging portion 312, the details of which will be discussed below. In one embodiment of the invention, the shaped recess 340 defined in the proximal head 322 includes connecting portions 342a, 342b and a receiving portion 344. In the illustrated embodiment of the invention, the connecting portion 342a comprises a cylindrical-shaped passage defining internal threads 343a adapted to threadingly receive a threaded end portion of the guiding portion 314. Similarly, the connecting portion 342b comprises a cylindrical-shaped passage generally aligned with the passage 342a and defining internal threads 343b adapted to threadingly receive a threaded end portion of an instrument therein, the details of which will be discussed below.

Figure 11:
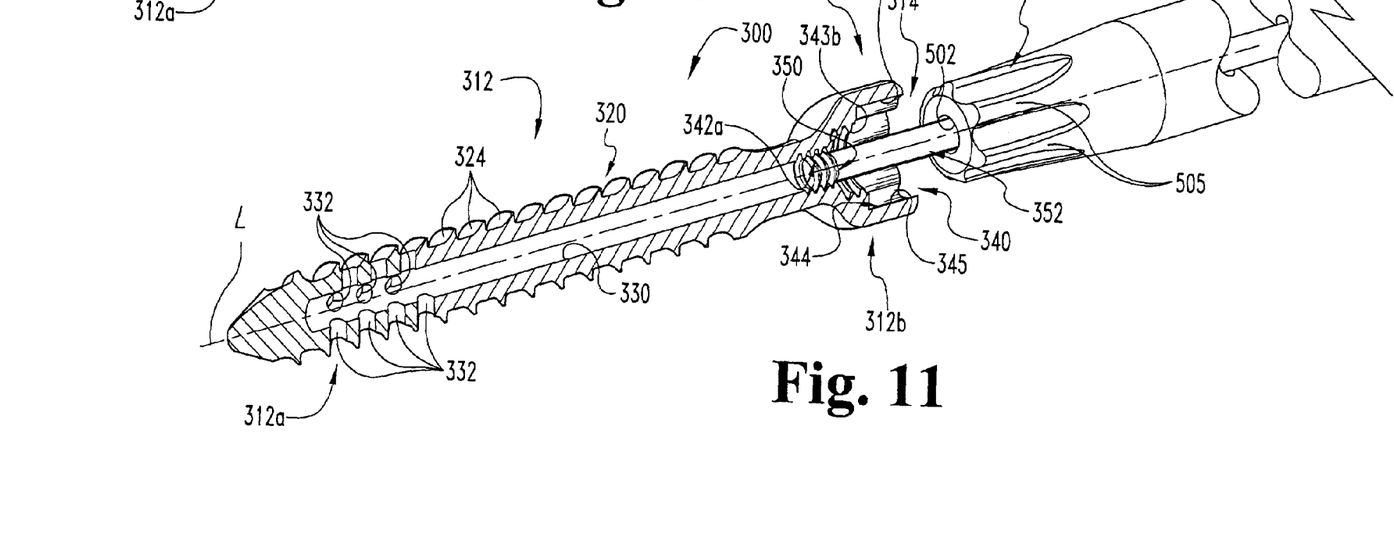
FIG. 11 is a partial cross-sectional perspective view of the bone anchor illustrated in FIG. 8, with a driver instrument being guided toward the bone engaging portion of the bone anchor along an elongate guiding portion of the bone anchor.

In another embodiment of the invention, the receiving portion 344 defined by the proximal head 322 comprises an axially-extending receptacle or opening sized to engagingly receive a correspondingly shaped end portion of an instrument, implant, mechanism, and/or other types of elements therein. In the illustrated embodiment of the invention, the receiving portion 344 has a Torx™-type configuration, including a number of recessed areas or axial grooves 345 spaced uniformly about the interior of the receiving portion 344. The axial grooves 345 are configured to receive axially-extending projections or splined portions 505 spaced uniformly about the exterior of the distal end portion 504 of a driver instrument 500 (FIG. 11). However, it should be understood that the receiving portion 344 may take on other shapes and configurations, including a hexagonal shape, a circular or elliptical shape, a square or rectangular shape, or any other shape or configuration that would occur to one of skill in the art.

In one embodiment of the invention, the elongate guiding portion 314 comprises a shaped end portion 350 and an elongate shaft portion 352 extending therefrom. In the illustrated embodiment, the shaped end portion 350 has a cylindrical-shaped configuration defining external threads 351 adapted for engagement within the internally threaded passage 342a defined in the proximal head 322 of the bone engaging portion 312. As should be appreciated, the threading engagement between the externally threaded end portion 350 and the internally threaded passage 342a releasably engages the elongate guiding portion 314 to the bone engaging portion 312 and also allows for selective removal of the elongate guiding portion 314 therefrom. The distally-facing surface of the threaded end portion 350 may be tapered to facilitate insertion into and threading engagement with the threaded passage 342a.

Similar to the elongate shaft portion 152 illustrated and described above with regard to the bone anchor 100, the elongate shaft portion 352 extends from the threaded end portion 350 and is adapted to guide or direct various devices, instruments, implants and/or other elements toward the proximal head 322 of the bone engaging portion 312. For example, as shown in FIG. 9, the elongate shaft 352 of the guiding portion 314 may be used to guide a tubular member 400 into engagement with the proximal head 322 of the bone engaging portion 312. More specifically, the tubular member 400 may be engaged to the guiding portion 314 of the bone anchor 300 at a location outside of the patient's body via insertion of the proximal end portion of the shaft 352 into the axial passage 402 of the tubular member 400. The elongate shaft 352 may then be used to guide the tubular member 400 through a visually-obstructed opening and/or a relatively narrow tissue protection device to facilitate engagement of the distal end portion 404 of the tubular member 400 with the proximal head 322 of the bone anchor 300.

In one embodiment of the invention, the distal end portion 404 of the tubular member 400 defines external threads 405 adapted for engagement within the internally threaded passage 342b defined in the proximal head 322 of the bone engaging portion 312. As should be appreciated, the threading engagement between the threaded distal end portion 404 and the internally threaded passage 342b releasably engages the tubular member 400 to the bone engaging portion 312 and also allows for selective removal of the tubular member 400 from the bone engaging portion 312. The distally-facing surface of the threaded distal end portion 404 may be tapered to facilitate insertion into and threading engagement with the threaded passage 342b.

Figure 10:
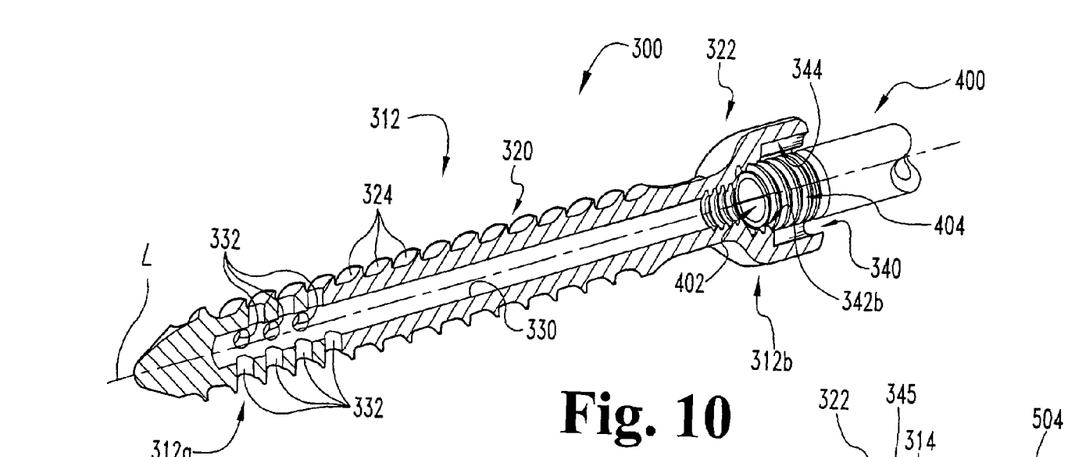
FIG. 10 is a partial cross-sectional perspective view of the bone anchor illustrated in FIG. 9, with the elongate guiding portion removed therefrom and with injector tube coupled to the bone engaging portion of the bone anchor.

Referring to FIG. 10, when the threaded distal end portion 404 is engaged within the threaded passage 342b, the axial passage 402 of the tubular member 400 is positioned in communication with the cannula passage 330 in the bone engaging portion 312. Material may then be conveyed through the axial passageway 402 in the tubular member 400 for delivery to the cannula passage 330 and out the fenestration openings 332 to a location laterally adjacent the bone engaging portion 312. Notably, delivery of the material to the cannula passage 330 may be made via a delivery system or injector mechanism located remote from the proximal head 322 of the bone engaging portion 312, and possibly from a location entirely outside of the patient's body. As discussed above, such material may include bone cement, a bone growth promoting substance such as BMP, or other types of bio-compatible materials.

Referring to FIG. 11, in a further embodiment of the invention, the elongate shaft 352 of the guiding portion 314 may be used to guide a driver instrument 500 into engagement with the proximal head 322 of the bone engaging portion 312. As discussed above, the driver instrument 500 includes a distal end portion 504 having a Torx™-type configuration defining a number of axially-extending projections or splined portions 505 for receipt within the recessed areas or axial grooves 345 defined within the receiving portion 344 of the proximal head 322 to facilitate driving of the bone engaging portion 312 into and/or out of bone. The driver instrument 500 also defines an axial passage 502 extending at least partially therethrough and sized to receive the elongate shaft 352 of the guiding portion 314 therein. As should be appreciated, the driver instrument 500 may be engaged with the proximal end portion of the elongate shaft 352 at a location outside of the patient's body via insertion of the proximal end portion of the shaft 352 into the axial passage 502. The elongate shaft 352 may then be used to guide the distal end portion 504 of the driver instrument 500 into engagement with the proximal head 322 of the bone anchor 300. Such guiding may be particularly useful when attempting to engage the driver instrument 500 with the bone engaging portion 312 of the bone anchor 300 through a visually-obstructed opening and/or a relatively narrow tissue protection device.

Figure 12:
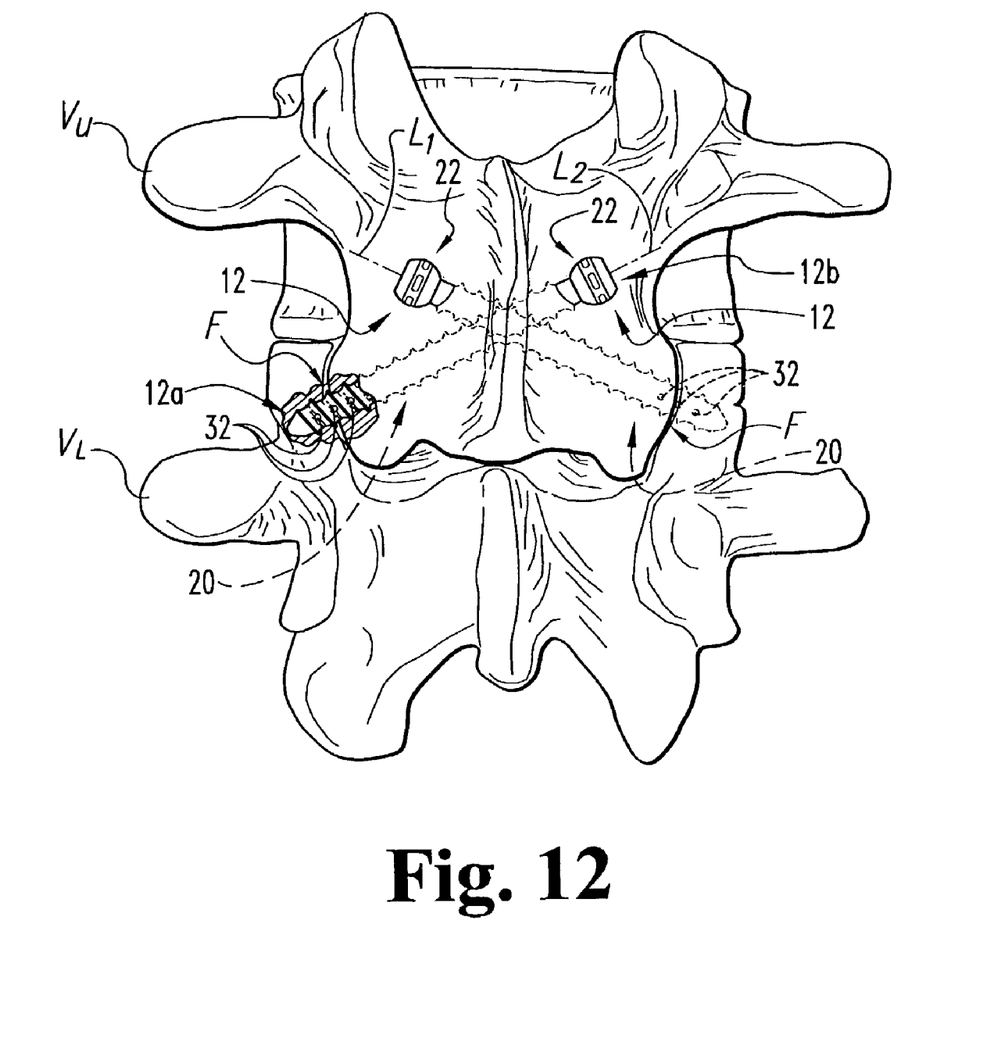
FIG. 12 is a posterior view of a portion of the spinal column, illustrating engagement of a pair of bone anchors across the facet joints defined between upper and lower vertebrae.

Referring to FIG. 12, shown therein is a pair of the bone screws 12 engaged to a portion of the spinal column. More specifically, the threaded shank portions 20 of the bone screws 12 are engaged across the facet joints F of the upper and lower vertebrae $V_U$, $V_L$, with the longitudinal axis $L_1$, $L_2$, of the bone screws 12 arranged in a transverse or X-shaped configuration (when viewed from an anterior-posterior direction). The bone screws 12 thereby serve to interconnect or join the upper and lower vertebrae $V_U$, $V_L$. However, it should be understood that the bone screws 12 may be engaged across the facet joints F via other techniques to secure the facet joints F together and to interconnect the upper and lower vertebrae $V_U$, $V_L$. As would occur to those of skill in the art, such fixation techniques are used to treat diseased or injured spinal motion segments. As would also occur to those of skill in the art, this type of treatment may also be done in combination with various types of interbody fusion techniques.

In order to enhance fixation and/or fusion of the facet joints F, a material may be delivered to the areas adjacent the facet joints F, and more specifically to the areas adjacent the facet capsules defined by the facet joints F. Such material may include, for example, bone cement, a bone growth promoting substance such as BMP, or other bio-compatible materials know to those of skill in the art. Notably, when the bone screws 12 are properly anchored to the upper and lower vertebrae $V_U$, $V_L$, the fenestration openings 32 will be positioned adjacent the facet joints F, and more particularly adjacent the facet capsules. In this manner, material may be delivered through the cannula passage 30 extending through the threaded shank 20 of the screws 12 (FIGS. 2 and 3) and dispensed out the fenestration openings 32 to a targeted location adjacent the facet joints F. Since the fenestration openings 32 are strategically positioned along the distal end portions 12a of the bone screws 12, and more particularly along the distal-most one-third of the bone screws 12, delivery of the material to the facet joints F, and more particularly to the facet capsules, can be accomplished in a controlled and efficient manner.

While the invention has been illustrated and described in detail in the drawings and foregoing description, the same is to be considered as illustrative and not restrictive in character, it being understood that only the preferred embodiments have been shown and described, and that all changes and modifications that come within the spirit of the invention are desired to be protected.

What is claimed is:

1. A bone anchor, comprising:
   a bone engaging portion having a proximal end portion and a distal end portion, said bone engaging portion including a cannula passage extending at least partially therethrough from said proximal end portion toward said distal end portion and at least one transverse opening in communication with said cannula passage, said proximal end portion including a recess; and
   an elongate guiding portion including an end portion and a shaft portion extending axially from said end portion, said end portion received within said recess to engage said guiding portion with said bone engaging portion, said shaft portion having proximal end and a length extending outside of a patient's body when said bone engaging portion is engaged to bone, said length of said shaft portion extending outside of the patient's body having an outer transverse dimension sized smaller than an inner cross section of said recess to thereby define an annular passage between said shaft portion and an inner wall of said proximal end portion; and
   a device having a distal end defining a passage sized larger than an outer transverse dimension of said proximal end of said shaft portion, said proximal end of said shaft portion inserted into and through said passage to allow said distal end of said device to be guided along said shaft portion and into said annular passage, said annular passage sized larger than said distal end of said device, said distal end positioned within said annular passage to engage said device with said proximal end portion of said bone engaging portion.

2. The bone anchor of claim 1, wherein said cannula passage extends partially through said bone engaging portion.

3. The bone anchor of claim 1, wherein each of said at least one transverse opening is disposed along a distal end portion of said bone engaging portion.

4. The bone anchor of claim 3, wherein each of said at least one transverse opening is disposed along a distal-most one third of said bone engaging portion.

5. The bone anchor of claim 1, wherein said bone engaging portion defines a plurality of said at least one transverse opening in communication with said cannula passage.

6. The bone anchor of claim 1, wherein said end portion of said elongate guiding portion is configured to be releasably engaged within said recess in said proximal end portion of said bone engaging portion to allow selective removal of said elongate guiding portion from said bone engaging portion.

7. The bone anchor of claim 6, wherein said elongate guiding portion is configured to threadingly engage said bone engaging portion.

8. The bone anchor of claim 1, wherein said end portion of said elongate guiding portion is configured to be engaged within said recess in said proximal end portion of said bone engaging portion to allow angular displacement of sail elongate guiding portion relative to said bone engaging portion.

9. The bone anchor of claim 1, wherein said elongate guiding portion defines an axial passageway extending therethrough and communicating with said cannula passage; and
further comprising a material delivered from said axial passageway, into said cannula passage and out said at least one transverse opening.

10. The bone anchor of claim 1, wherein said end portion of said elongate guiding portion comprises a shaped end portion, and wherein said recess in said proximal end portion of said bone engaging portion comprises a shaped recess configured to receive said shaped end portion.

11. The bone anchor of claim 10, wherein said shaped end portion and said shaped recess each have an at least partially spherical configuration.

12. The bone anchor of claim 10, wherein said shaped end portion and said shaped recess each have an at least partially cylindrical configuration.

13. The bone anchor of claim 1, further comprising a material deliverable into said cannula passage and out said at least one transverse opening.

14. The bone anchor of claim 13, wherein said material comprises bone cement.

15. The bone anchor of claim 13, wherein said material comprises a bone growth promoting substance.

16. The bone anchor of claim 15, wherein said bone growth promoting substance comprises a bone morphogenic protein.

17. A bone anchor, comprising:
a bone engaging portion having a proximal end portion and a distal end portion, said bone engaging portion including a cannula passage extending at least partially therethrough from said proximal end portion toward said distal end portion and at least one transverse opening in communication with said cannula passage, said proximal end portion including a recess; and
an elongate guiding portion including an end portion and a shaft portion extending axially from said end portion, said end portion received within said recess to engage said guiding portion with said bone engaging portion, said shaft portion having an outer transverse dimension sized smaller than an inner cross section of said recess to thereby define an annular passage between said shalt portion and an inner wall of said proximal end portion, said annular passage sized to receive a distal end of a device guided into said annular passage by said shaft portion to engage said device with said proximal end portion; and
wherein said end portion of said elongate guiding portion comprises a spherical shaped ball and wherein said recess in said proximal end portion of said bone engaging portion comprises a spherical shaped socket.

18. The bone anchor of claim 17, wherein said spherical shaped ball is press fit into said spherical shaped socket to releasably engage said elongate guiding portion with said bone engaging portion.

19. A system, comprising:
a bone anchor including a bone engaging portion having a proximal end portion and a distal end portion, said bone engaging portion including a cannula passage extending at least partially therethrough from said proximal end portion toward said distal end portion and at least one transverse opening in communication with said cannula passage, said proximal end portion including a recess, said bone anchor further including an elongate guiding portion including an end portion and a shaft portion extending axially from said end portion, said end portion received within said recess to engage said guiding portion with said bone engaging portion, said shaft portion having a length extending outside of a patient's body when said bone engaging portion is engaged to bone, said length of said shaft portion extending outside of the patient's body having an outer transverse dimension sized smaller than an inner cross section of said recess to thereby define an annular passage between said shaft portion and an inner wall of said proximal end portion; and
a device having a distal end and a passage sized larger than said outer transverse dimension of said shaft portion for receipt of said shaft portion through said passage to allow said device to be guided along said shaft portion of said elongate guiding portion and into said annular passage, said annular passage sized to receive said distal end to engage said device with said proximal end portion of said bone engaging portion;
a material deliverable into said cannula passage and out said at least one transverse opening; and
wherein the device comprises an injector adapted to inject said material into said cannula passage and out said at least one transverse opening.

20. A bone anchor, comprising:
a bone engaging portion having a proximal end portion and a distal end portion, said proximal end portion including a recess; and
an elongate guiding portion including an end portion and a shaft portion extending axially from said end portion, said end portion received within said recess to engage said guiding portion with said proximal end portion of said bone engaging portion so as to allow rotational displacement of said end portion relative to said proximal end portion and angular displacement of said elongate guiding portion relative to said bone engaging portion, said shaft portion having a proximal end and a length extending outside of a patient's body when said bone engaging portion is engaged to bone, said length of said shaft portion extending outside of the patient's body having an outer transverse dimension sized smaller than an inner cross section of said recess to thereby define an annular passage between said shaft portion and an inner wall of said proximal end portion; and a device having a distal end defining a passage sized larger than an outer transverse dimension of said proximal end of said shaft portion, said proximal end of said shaft portion inserted into and through said passage to allow said distal end of said device to be guided along said shaft portion and into said annular passage, said annular passage sized larger than said distal end of said device, said distal end positioned within said annular passage to engage said device with said proximal end portion of said bone engaging portion.

21. The bone anchor of claim 20, wherein said end portion of said elongate guiding portion comprises a shaped end portion, said recess comprising a shaped recess configured to receive said shaped end portion so as to allow said rotational displacement and said angular displacement.

22. The bone anchor of claim 21, wherein said shaped end portion and said shaped recess each have an at least partially spherical configuration.

23. The bone anchor of claim 21, wherein said shaped end portion is configured for releasable engagement within said shaped recess so as to allow selective separation of said elongate guiding portion from said bone engaging portion.

24. The bone anchor of claim 20, wherein said bone engaging portion includes a cannula passage extending at least partially therethrough from said proximal end portion toward said distal end portion and at least one transverse opening in communication with said cannula passage.

25. A system, comprising:
a bone anchor including a bone engaging portion having a proximal end portion and a distal end portion, said bone engaging portion including a cannula passage extending at least partially therethrough from said proximal end portion toward said distal end portion and at least one transverse opening in communication with said cannula passage, said proximal end portion including a recess, said bone anchor further including an elongate guiding portion including an end portion and a shaft portion extending axially from said end portion, said end portion engagingly received within said recess to engage said guiding portion with said bone engaging portion, said shaft portion having a proximal end and a length extending outside of a patient's body when said bone engaging portion is engaged to bone, said length of said shaft portion extending outside of the patient's body having an outer transverse dimension sized smaller than an inner cross section of said recess to thereby define an annular passage between said shaft portion and an inner wall of said proximal end portion; and a device having a distal end defining a passage sized larger than an outer transverse dimension of said proximal end of said shaft portion, said proximal end of said shaft portion inserted into and through said passage to allow said distal end of said device to be guided along said shaft portion of said elongate guiding portion and into said annular passage, said annular passage sized to receive said distal end to engage said device with said proximal end portion of said bone engaging portion.

26. The bone anchor of claim 25, wherein the device comprises a surgical instrument.

27. The bone anchor of claim 25, wherein the device comprises a material delivery mechanism.

28. The bone anchor of claim 25, wherein said cannula passage extends partially through said bone engaging portion.

29. The bone anchor of claim 25, wherein each of said at least one transverse opening is disposed along a distal end portion of said bone engaging portion.

30. The bone anchor of claim 29, wherein each of said at least one transverse opening is disposed along a distal-most one third of said bone engaging portion.

31. The bone anchor of claim 25, wherein said bone engaging portion defines a plurality of said at least one transverse opening in communication with said cannula passage.

32. The bone anchor of claim 25, wherein said end portion of said elongate guiding portion is configured to be releasably engaged within said recess in said proximal end portion of said bone engaging portion to allow selective removal of said elongate guiding portion from said bone engaging portion.

33. The bone anchor of claim 25, wherein said end portion of said elongate guiding portion is configured to be engaged within said recess in said proximal end portion of said bone engaging portion to allow angular displacement of said elongate guiding portion relative to said bone engaging portion.

34. The bone anchor of claim 25, wherein said elongate guiding portion defines an axial passageway extending therethrough and communicating with said cannula passage; and
further comprising a material delivered from said axial passageway, into said cannula passage and out said at least one transverse opening.

35. The bone anchor of claim 25, wherein said end portion of said elongate guiding portion comprises a shaped end portion, and wherein said recess in said proximal end portion of said bone engaging portion comprises a shaped recess configured to receive said shaped end portion.

36. The bone anchor of claim 35, wherein said shaped end portion and said shaped recess each have an at least partially spherical configuration.

37. The bone anchor of claim 25, further comprising a material deliverable into said cannula passage and out said at least one transverse opening.

38. The bone anchor of claim 37, wherein the device comprises a tubular member adapted to convey said material into said cannula passage and out said at least one transverse opening.

39. The bone anchor of claim 38, wherein said tubular member is adapted to threadingly engage said proximal end portion of said bone engaging portion.

40. The bone anchor of claim 37, wherein said material comprises bone cement.

41. The bone anchor of claim 37, wherein said material comprises a bone growth promoting substance.

42. The bone anchor of claim 25, wherein said elongate guiding portion is sized to extend outside of a patient's body when said bone engaging portion is engaged to bone.

43. A system, comprising:
a bone anchor including a bone engaging portion having a proximal end portion and a distal end portion, said bone engaging portion including a cannula passage extending at least partially therethrough from said proximal end portion toward said distal end portion and at least one transverse opening in communication with said cannula passage, said proximal end portion including a recess, said bone anchor further including an elongate guiding portion including an end portion and a shaft portion extending axially from said end portion, said end portion received within said recess to engage said guiding portion with said bone engaging portion, said shaft portion having an outer transverse dimension sized smaller than an inner cross section of said recess to thereby define an annular passage between said shaft portion and an inner wall of said proximal end portion; and a device having a distal end configured to be guided along said shaft portion of said elongate guiding portion and into said annular passage, said annular passage sized to receive said distal end to engage said device with said proximal end portion of said bone engaging portion; and wherein said end portion of said elongate guiding portion comprise a spherical shaped ball and wherein said recess in said proximal end portion of said bone engaging portion comprises a spherical shaped socket.

44. The bone anchor of claim 43, wherein said spherical shaped ball is press fit into said spherical shaped socket to releasably engage said elongate guiding portion with said bone engaging portion.

* * * * *